United States Patent [19]

Saville

[11] Patent Number: Plant 7,448

[45] Date of Patent: Feb. 19, 1991

[54] MINIATURE ROSE PLANT NAMED SAVARAIN

[75] Inventor: F. Harmon Saville, Rowley, Mass.

[73] Assignee: Nor'East Miniature Roses, Inc., Rowley, Mass.

[21] Appl. No.: 410,308

[22] Filed: Sep. 20, 1989

[51] Int. Cl.[5] ..... A01H 5/00

[52] U.S. Cl. ..... Plt./7

[58] Field of Search ..... Plt. 7, 9, 10, 22

*Primary Examiner*—Howard J. Locker

*Attorney, Agent, or Firm*—Christie, Parker & Hale

[57] ABSTRACT

A new and unusual lavender toned miniature rose.

1 Drawing Sheet

SUMMARY OF THE INVENTION

The present invention relates to a new and distinct variety of rose plant of the miniature rose class, which was originated by my crossing as seed parent the variety known as "Sachet" (U.S. Plant Pat. No. 5,967) and as pollen parent the variety known as "Rainbow's End" (U.S. Plant Pat. No. 5,482). The varietal denomination of this new rose is "Savarain."

Among the novel characteristics possessed by this new variety which distinguishes it from its parents and all other varieties of which I am aware are its unusual lavendar toned flowers in this class of rose. Flowers open well and retain multi-lavender tones which lighten as blooms age. Asexual reproduction by propagation by cuttings of the new variety as performed in Essex County, Mass., shows that the foregoing and other distinguishing characteristcs come true to form and are established and transmitted through succeeding propagations.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Colour Chart (RHSCC). The terminology used in color description herein refers to plate numbers in the aforementioned color chart, e.g., "186A" is place 186A of The Royal Horticultural Society Colour Chart.

Parentage: Seedling.

*Seed parent.*—"Sachet".

*Pollen parent.*—"Rainbow's End".

Class: Miniature.

The following observations are made of specimens grown outdoors in Essex County, Mass., during the month of July.

FLOWER

Blooming habit: Continuous.

A. Bud:

(1) *Size.*—Small.

(2) *Form.*—Ovate.

(3) *Color.*—As sepals divide, bud color is near 186A to B.

(4) *Sepals.*—About same length as bud.

(5) *Peduncle.*—Length — about $\frac{5}{8}$ inch. Aspect — straight. Strength — erect. Color — near 146C.

B. Bloom:

(1) *Size.*—Average size when fully — about $1\frac{1}{2}$ inch.

(2) *Borne.*—Sometimes singly, one to a stem, but usually in sprays of 5 to 20 blooms.

(3) *Form.*—High centered at first, becoming flat. Petals reflex mildly quill to points or roll under.

(4) *Petalage.*—Number of petals under normal conditions — about 24.

(5) *Color.*—After sepals fall and petals unfurl, predominant flower color viewing petals' top surface are multi-lavendar tones, ranging from near 186A to B at petals' outer margins and edges washing and blending into lighter tones, near 186C to D toward flower centers. Top surfaces of inner petals tend to be lighter toned, near 186C to D, becoming mostly 186D or slightly lighter. Petal undersurfaces display similar deeper lavendar tones in outer petals tending to lighten in inner petals. Individual petals, top and bottom surfaces, may show washing or diffusing of lighter tones into deeper toned coloring, and vice versa. General tonality viewed at a distance is attractive multi-toned lavender. Color at point of petal attachment is near 2C.

C. Petals:

(1) *Texture.*—Medium.

(2) *Appearance.*—Inside velvety and outside satiny.

(3) *Form.*—Broad, fan shaped with pointed apices.

(4) *Arrangement.*—Regularly arranged, imbricated.

(5) *Petal in center.*—Few.

(6) *Persistence.*—Drop off cleanly.

(7) *Fragrance.*—Slightly.

(8) *Lasting quality.*—Average lasting quality on plant and as cut flower.

REPRODUCTIVE ORGANS

A. Stamens, filaments and anthers:

*Arrangement and color.*—Regularly arranged around styles. Color — filaments near 163B.

B. Pollen:

*Color.*—Near 163D.

C. Styles: Medium length, thin.

D. Stigmas:

*Color.*—Near 9D.

E. Hips: None observed.

PLANT

A. Form: Upright.

B. Growth: Vigorous.

*Height attained.*—About 14 to 16 inches.

C. Foliage: Compound 5 to 7 leaflets.

(1) *Size.*—Medium.

(2) *Quantity.*—Abundant.

(3) *Color.*—New foliage: Upper side — near 138B. Under side — near 148C. Old foliage: Upper side — near 137A. Under side — near 137C.

(4) *Shape.*—Oval, pointed.

(5) *Texture.*—Upper side is semi-glossy; under side is matte.

(6) *Edge.*—Serrate.

(7) *Serration.*—Ordinary.

(8) *Leaf stem.*—Color — medium green. Under side — medium green.

(9) *Stipules.*—Fine, even.

(10) *Resistance to disease.*—Blackspot — Average. Mildew — Average. Rust — Average.

D. Wood:

(1) *New wood.*—Color — near 144B. Bark — smooth.

(2) *Old wood.*—Color — near 144A. Bark — smooth.

E. Thorns:

(1) *Thorns.*—Quantity (main stalk) — Ordinary. On laterals from stalk — few. Form — Thin, straight. Length — medium. Color — near 195C. Position — irregular.

(2) *Prickles.*—None.

F. Winter hardiness: Needs protection in severe climates.

I claim:

1. A new and distinct variety of rose plant of the miniature rose class, substantially as shown and described, characterized particularly by attractive lavendar toned flowers.

* * * * *

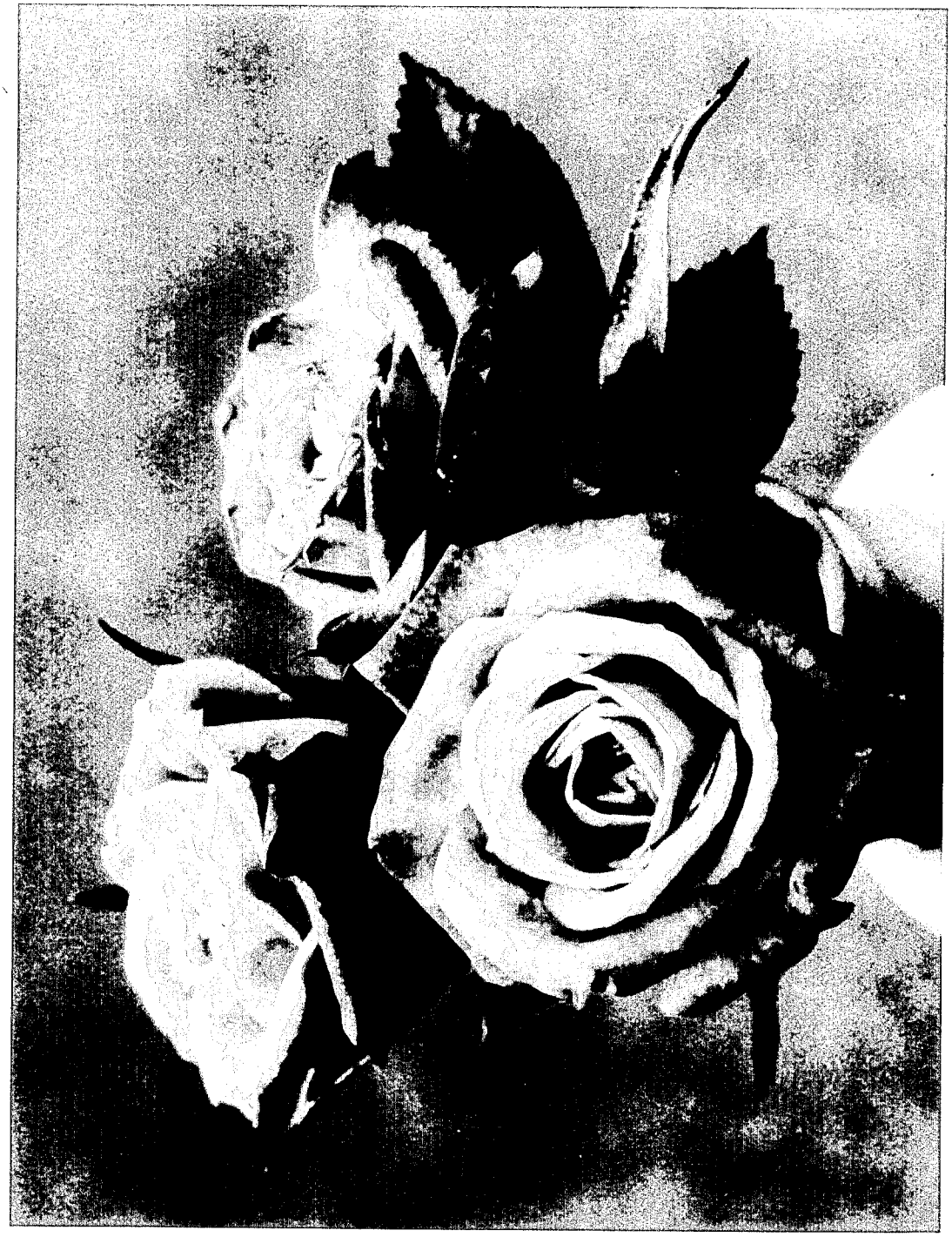

UNITED STATES PATENT AND TRADEMARK OFFICE

CERTIFICATE OF CORRECTION

PATENT NO. : Plant 7,448

DATED : February 19, 1991

INVENTOR(S) : F. Harmon Saville

It is certified that error appears in the above-identified patent and that said Letters Patent is hereby corrected as shown below:

Column 2, line 7, insert -- 1. -- before "FLOWER".
Column 2, line 18, after "fully" insert -- expanded --.

Column 3, line 9, change "slightly" to -- slight --.
Column 3, line 13, insert -- 2. -- before "REPRODUCTIVE ORGANS".
Column 3, line 25, insert -- 3. -- before "PLANT".

Signed and Sealed this

Twentieth Day of October, 1992

*Attest:*

DOUGLAS B. COMER

*Attesting Officer*

*Acting Commissioner of Patents and Trademarks*